United States Patent [19]

Clough et al.

[11] Patent Number: 4,994,495

[45] Date of Patent: Feb. 19, 1991

[54] FUNGICIDES

[75] Inventors: John M. Clough, Buckinghamshire; Christopher R. A. Godfrey, Bracknell; Paul J. de Fraine, Wokingham; Michael G. Hutchings, Bury; Ian Ferguson, Todmorde, all of England

[73] Assignee: Imperial Chemical Industries PLC, London, England

[21] Appl. No.: 350,344

[22] Filed: May 11, 1989

[30] Foreign Application Priority Data

May 13, 1988 [GB] United Kingdom ............... 8811435

[51] Int. Cl.$^5$ ...................... A01N 17/40; C07C 69/76
[52] U.S. Cl. .................... 514/574; 514/517; 514/521; 514/532; 514/539; 558/14; 558/15; 558/16; 558/48; 558/51; 558/389; 558/394; 558/396; 558/397; 560/9; 560/11; 560/12; 560/21; 560/34; 560/35; 560/42; 560/45; 560/53; 560/60
[58] Field of Search ................... 560/9, 11, 12, 21, 34, 560/35, 42, 45, 53, 60; 558/14, 15, 16, 48, 51, 389, 394, 396, 397; 514/574, 517, 521, 539, 532

[56] References Cited

U.S. PATENT DOCUMENTS

| 4,709,078 | 11/1987 | Schirmer et al. | 560/60 |
| 4,822,908 | 4/1989 | Karbach et al. | 560/60 |
| 4,895,974 | 1/1990 | Crowley | 560/60 |
| 4,937,374 | 6/1990 | Beautement et al. | 560/60 |

FOREIGN PATENT DOCUMENTS

| 0178826 | 4/1986 | European Pat. Off. | 560/60 |
| 0291196 | 11/1988 | European Pat. Off. | 560/60 |
| 0307101 | 3/1989 | European Pat. Off. | 560/60 |
| 0341845 | 11/1989 | European Pat. Off. | 560/60 |
| 3620860 | 12/1987 | Fed. Rep. of Germany | 560/60 |

Primary Examiner—Bruce Gray
Attorney, Agent, or Firm—Cushman, Darby & Cushman

[57] ABSTRACT

Fungicidal compounds having the formula:

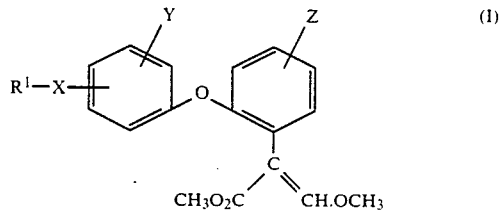

and stereoisomers thereof, wherein $R^1$ is optionally substituted $C_{2-10}$ alkenyl, optionally substituted $C_{5-6}$ cycloalkenyl, optionally substituted $C_{2-10}$ alkynyl, or $C_{1-10}$ alkyl substituted with —CN, —NC, —COR$^2$, —CO$_2$R$^2$, —NO$_2$ or —SCN; X is O, S(O)n or NR$^2$ and is attached to the 3- or the 4-position of the phenyl ring; Y and Z, which may be the same or different, are H, halogen, —CH$_3$, —C$_2$H$_5$, or —OCH$_3$; $R^2$ is H, $C_{1-4}$ alkyl, $C_{1-4}$ alkenyl, or, when $R^2$ is $C_{1-4}$ alkyl in the group —COR$^2$, it joins with the alkyl group to which —COR$^2$ is attached to form a 5- or 6-membered aliphatic ring; and n is 0, 1 or 2.

7 Claims, No Drawings

FUNGICIDES

This invention relates to derivatives of propenoic acid useful as fungicides, to processes for preparing them, to fungicidal compositions containing them, and to methods of using them to combat fungi, especially fungal infections in plants.

According to the present invention there is provided a compound having the formula (I):

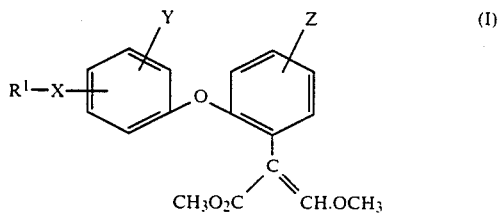

and stereoisomers thereof, wherein $R^1$ is optionally substituted $C_{2-10}$ alkenyl, optionally substituted $C_{5-6}$ cycloalkenyl, optionally substituted $C_{2-10}$ alkynyl, or $C_{1-10}$ alkyl substituted with —CN, —NC, —COR$^2$, —CO$_2$R$^2$, —NO$_2$ or —SCN; X is O, S(O)n or NR$^2$ and is attached to the 3- or the 4-position of the phenyl ring; Y and Z, which may be the same or different, are H, halogen, —CH$_3$, —C$_2$H$_5$, or —OCH$_3$; $R^2$ is H, $C_{1-4}$ alkyl, $C_{1-4}$ alkenyl, or, when $R^2$ is $C_{1-4}$ alkyl in the group —COR$^2$, it joins with the alkyl group to which —COR$^2$ is attached to form a 5- or 6-membered aliphatic ring; and n is 0, 1 or 2.

The compounds of the invention contain at least one carbon-carbon double bond, and are sometimes obtained in the form of mixtures of geometric isomers. However, these mixtures can be separated into individual isomers, and this invention embraces such isomers, and mixtures thereof in all proportions.

The individual isomers which result from the unsymmetrically substituted double bond of the propenoate group are hereinafter identified by the commonly used terms "E" and "Z". These terms are defined according to the Cahn-Ingold-Prelog system which is fully described in the literature (see, for example, J. March, "Advanced Organic Chemistry", 3rd edition, Wiley-Interscience, page 109 et seq).

Usually one isomer is more active fungicidally than the other, the more active isomer usually being the one wherein the groups —CO$_2$CH$_3$ and —OCH$_3$ are on opposite sides of the olefinic bond of the propenoate group (the (E)-isomer). These (E)-isomers form a preferred embodiment of the invention.

Substituents which may be present in the optionally substituted alkenyl or alkynyl moieties include one or more of the following: halogen, hydroxy, $C_{1-4}$ alkoxy, halo($C_{1-4}$)alkyl (especially trifluoromethyl), halo($C_{1-4}$)alkoxy (especially trifluoromethoxy), $C_{1-4}$ alkylthio (especially methylthio), cyano, thiocyanato, nitro, —NR'R", —NHCOR', —NHCONR'R", —CONR'R", —COOR', —OSO$_2$R', —SO$_2$R', —COR', —CR'=NR" or —N=CR'R" in which R' and R" are independently hydrogen or $C_{1-4}$ alkyl.

The invention is illustrated by the compounds listed in Table I. Throughout Table I the methyl 3-methoxypropenoate group has the (E)-configuration.

TABLE I

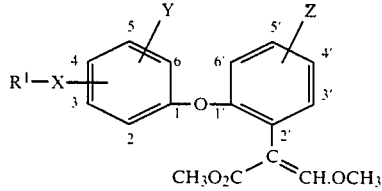

| Compound No. | R$^1$X | Y | Z | Olefinic | Melting Point (°C.) |
|---|---|---|---|---|---|
| 1 | 3-(CH$_2$=CH.CH$_2$)O— | H | H | 7.47 | Gum |
| 2 | 3-(HC≡C.CH$_2$)O— | H | H | 7.45 | Gum |
| 3 | 4-(CH$_2$=CH.CH$_2$)O— | H | H | 7.41 | 80-81 |
| 4 | 4-(HC≡C.CH$_2$)O— | H | H | 7.42 | 107-107.5 |
| 5 | 3-(CH$_2$=CH.CH$_2$)SO$_2$— | H | H | | |
| 6 | 4-(HC≡C.CH$_2$)S— | H | H | | |
| 7 | 3-(CH$_2$=CH.CH$_2$)NH— | H | H | | |
| 8 | 4-(CH$_2$=CH.CH$_2$)NCH$_3$— | H | H | | |
| 9 | 3-(N≡C.CH$_2$)O— | H | H | 7.48 | Gum |
| 10 | 4-(N≡C.CH$_2$)O— | H | H | 7.51 | Gum |
| 11 | 3-(CH$_3$O$_2$C.CH$_2$)O— | H | H | 7.48 | 75-77 |
| 12 | 4-(C$_2$H$_5$O$_2$C.CH$_2$)O— | H | H | | |
| 13 | 3-(C=N.CH$_2$)O— | H | H | | |
| 14 | 4-(C=N.CH$_2$)O— | H | H | | |
| 15 | 3-(OHC.CH$_2$)O— | H | H | | |
| 16 | 4-(OHC.CH$_2$)O— | H | H | | |
| 17 | 3-(O$_2$N.CH$_2$.CH$_2$)O— | H | H | | |
| 18 | 4-(O$_2$N.CH$_2$CH$_2$)O— | H | H | | |
| 19 | 3-(NCS.CH$_2$CH$_2$)O— | H | H | 7.48 | Gum |
| 20 | 3-(CH$_2$=CH.CH$_2$)O— | 4-Cl | H | | |
| 21 | 4-(CH$_2$=CH.CH$_2$)O— | 2-CH$_3$O | H | | |
| 22 | 3-(HC≡C.CH$_2$)O— | 4-Br | H | | |
| 23 | 4-(HC≡C.CH$_2$)O— | 3-F | H | | |
| 24 | 3-(CH$_2$=CH.CH$_2$)O— | H | 4'-F | | |
| 25 | (E)-3-(CH$_3$.CH=CH.CH$_2$)O— | H | H | | |
| 26 | (Z)-4-(CH$_3$.CH=CH.CH$_2$)O— | H | H | | |
| 27 | 3-(HC=C.CH$_2$CH$_2$)O— | H | H | | |
| 28 | 4-(CH$_2$=CH.CH$_2$CH$_2$)O— | H | H | | |

TABLE I-continued

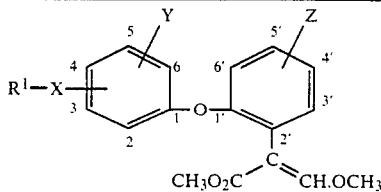

| Compound No. | R¹X | Y | Z | Olefinic* | Melting Point (°C.) |
|---|---|---|---|---|---|
| 29 | 3-[cyclohexenyl-O-] | H | H | 7.48 | Oil |
| 30 | 3-(CH₃O₂C.CH₂CH₂)O— | H | H | | |
| 31 | 4-(N≡C.CH₂CH₂)O— | H | H | | |
| 32 | 3-(OHC.CH₂CH₂)O— | H | H | | |
| 33 | 3-(CH₃CO—CH₂CH₂O— | H | H | | |
| 34 | 3-[3-oxocyclohexyl-O-] | H | H | | |
| 35 | (E)-3-(CH₃O₂C.CH=CH)O— | H | H | | |
| 36 | (Z)-3-(CH₃O₂C.CH=CH)O— | H | H | | |
| 37 | 3-(CH₂=CH.(CH₂)₄)O— | H | H | | |
| 38 | 3-[(CH₃)₂C=CH.CH₂]O— | H | H | 7.50 | Gum |
| 39 | 3-HC≡C.CH₂NH— | H | H | 7.47 | Gum |
| 40 | 3-CH₃CO.CH₂O— | H | H | 7.48 | Gum |
| 41 | 3-CH₃CH₂O.COCH₂O— | H | H | 7.48 | Gum |
| 42 | 3-O₂N.CH₂O— | H | H | | |

*Chemical shift of singlet from olefinic proton on beta-methoxypropenoate group (ppm from tetramethylsilane).
Solvent: CDCl₃ unless otherwise stated.

TABLE II

SELECTED PROTON n.m.r. DATA

| COMPOUND NO. | ppm. |
|---|---|
| 2 | (250 MHz) 2.61 (1H,t), 3.62 (3H,s), 3.79 (3H,s), 4.65(2H,d), 6.57-7.3 (8H,m), 7.45 (1H,s) ppm. |
| 9 | (90 MHz) 3.63 (3H,s), 3.78 (3H,s), 4.73 (2H,s), 6.5-6.8 (3H,m), 6.9-7.5 (5H,m), 7.48 (1H,s)ppm. |
| 10 | (90 MHz) 3.65 (3H,s), 3.80 (3H,s), 4.75 (2H,s), 6.96 (5H,s), 7.1-7.4 (3H,m), 7.51 (1H,s) ppm. |
| 19 | (270 MHz) 3.61 (3H,s), 3.78 (3H,s), 5.35 (2H,s) 6.60-6.71 (3H,m), 6.96-7.01 (1H,m), 7.11-7.33 (4H,m), 7.48 (1H,s) ppm. |
| 29 | (270 MHz) 1.5-2.2 (6H,m), 3.62 (3H,s), 3.76 (3H,s), 4.73 (1H, brs), 5.78-5.87 (1H, m) 5.92-6.01 (1H,m), 6.48-6.66 (3H,m), 6.92-6.99 (1H,m), 7.09-7.20 (2H,m), 7.22-7.32 (2H,m), 7.48 (1H,s) ppm. |
| 38 | (90 MHz) 1.55-1.80 (6H,m), 3.63 (3H,s), 3.78 (3H,s), 4.45 (2H, brd), 5.3-5.6 (1H,m), 6.4-6.7 (3H,m), 6.9-7.4 (5H,m), 7.50 (1H,s) ppm. |
| 40 | (270 MHz) 2.26 (3H,s), 3.61 (3H,s), 3.78 (3H,s), 4.49 (2H,s), 6.50-6.61 (3H,m), 6.94-6.99 (1H,m) 7.11-7.20 (2H,m), 7.25-7.32 (2H,m), 7.48 (1H,s) |

Table II shows selected proton n.m.r data for certain compounds described in Table I. Chemical shifts are measured in ppm from tetramethylsilane, and deuterochloroform was used as solvent throughout. The following abbreviations are used:
br = broad
s = singlet
d = doublet
t = triplet
q = quartet
m = multiplet
ppm = parts per million
n.m.r. = nuclear magnetic resonance The compounds of the invention of formula (I) can be made by a variety of methods, and some of these are illustrated in Schemes I to V. Throughout these Schemes, the terms X, Y, Z, R¹ and R² are as defined above, R³ is hydrogen or a metal (such as sodium or potassium), R is an alkyl group, and L is a leaving group such as a halide (chloride, bromide or iodide), a CH₃SO₄-anion, or a sulphonyloxy-anion. Each of the transformations described in Schemes I to V is performed at a suitable temperature and either in a suitable solvent or in the absence of a solvent.

Scheme I illustrates ways in which the methyl beta-methoxypropenoate group can be constructed in the final stages of the preparation of the compounds of the invention from appropriately substituted precursors. Alternatively, the methyl betamethoxypropenoate group may be constructed at an earlier stage of the preparation, in which case the final step or steps comprise elaboration of other parts of the compounds of the invention. Examples of procedures of this kind are shown in Schemes III to V.

In whichever order the steps are carried out to prepare the compounds of the invention, the diphenyl ether linkage which is common to all the compounds of the invention can be prepared by one of the coupling reactions shown in Scheme II. For a review of the Ullmann ether synthesis see A. A. Moroz and M. S. Shrartsberg, *Russian Chem.Reviews*, 1974, 43, 679. These couplings are often performed in the presence of a catalyst which consists of a transition metal or a salt of a transition metal, such as copper or a copper salt. In Scheme II, the term W represents either the group $R^1$—X—, wherein $R^1$ and X are as defined above, or a group which can be converted by standard procedures described in the chemical literature into the group $R^1$—X—; and the term A represents either the alpha-linked methyl betamethoxypropenoate group of the compounds of the invention or a group which can be converted into such a group by standard methods described in the chemical literature and/or described in Scheme I and the following paragraphs. In the context of Scheme II, the term L is preferably a halogen.

The compounds of the invention of formula (1) can be prepared from the phenylacetates of formula (III) or the ketoesters of formula (VI) by the steps shown in Scheme I.

Thus compounds of formula (I) can be prepared by treatment of phenylacetates of formula (III) with a base (such as sodium hydride or sodium methoxide) and methyl formate. If a species of formula $CH_3L$, wherein L is as defined above, is then added to the reaction mixture, compounds of formula (I) may be obtained. If a protic acid is added to the reaction mixture, compounds of formula (II) wherein $R^3$ is hydrogen are obtained. Alternatively, the species of formula (II) wherein $R^3$ is a metal (such as sodium) may themselves be isolated from the reaction mixture.

Compounds of formula (II) wherein $R^3$ is a metal can be converted into compounds of formula (I) by treatment with a species of formula $CH_3L$, wherein L is as defined above. Compounds of formula (II) wherein $R^3$ is hydrogen can be converted into compounds of formula (I) by successive treatments with a base (such as potassium carbonate) and a species of general formula $CH_3L$.

Alternatively, compounds of formula (I) can be prepared from acetals of formula (IV) by elimination of methanol under either acidic or basic conditions. Examples of reagents or reagent mixtures which can be used for this transformation are lithium diisopropylamide; potassium hydrogen sulphate (see, for example, T. Yamada, H. Hagiwara and H. Uda, *J.Chem.Soc., Chemical Communications*, 1980, 838, and references therein); and triethylamine, often in the presence of a Lewis acid such as titanium tetrachloride (see, for example, K. Nsunda and L. Heresi, *J.Chem.Soc., Chemical Communications*, 1985, 1000).

Acetals of formula (IV) can be prepared by treatment of methyl silyl ketene acetals of formula (V) wherein R is an alkyl group, with trimethyl orthoformate in the presence of a Lewis acid such as titanium tetrachloride (see, for example, K. Saigo, M. Osaki and T. Mukaiyama, *Chemistry Letters*, 1976, 769).

Methyl silyl ketene acetals of formula (V) can be prepared from phenylacetates of formula (III) by treatment with a base and a trialkylsilyl halide of formula $R_3SiCl$ or $R_3SiBr$, such as trimethylsilyl chloride, or a base (such as triethylamine) and a trialkylsilyl triflate of formula $R_3Si$—$OSO_2CF_3$ (see, for example, C. Ainsworth, F. Chen and Y. Kuo, *J.Organometallic Chemistry*, 1972, 46, 59).

It is not always necessary to isolate the intermediates (IV) and (V); under appropriate conditions, compounds of formula (I) may be prepared from phenylacetates of formula (III) in "one pot" by the successive addition of suitable reagents listed above.

Alternatively, compounds of formula (I) can be prepared by treatment of ketoesters of formula (VI) with, for example, methoxymethylenetriphenylphosphorane (see, for example, W. Steglich, G. Schramm, T. Anke and F. Oberwinkler, EP 0044448, 4.7.1980).

Ketoesters of formula (VI) may be prepared by methods described in the literature. Particularly useful methods include (i) the reaction of appropriate phenylmagnesium halides or phenyl-lithium species with dimethyl oxalate using the method described by L. M. Weinstock, R. B. Currie and A. V. Lovell, *Synth.Commun.*, 1981, 11, 943 and references therein: (ii) oxidation of phenylacetates of formula (III) using selenium dioxide, generally in the absence of a solvent, and generally at a temperature above 100° C.; and (iii) oxidation of mandelic acid esters using, for example, manganese oxide in a suitable solvent.

Phenylacetates of formula (III) and the corresponding phenylacetic acids of formula (VII) may also be prepared by numerous other methods described in the chemical literature. For example, several useful methods are described by D. C. Atkinson, K. E. Godfrey, B. Meek, J. F. Saville and M. R. Stillings, *J.Med.Chem.*, 1983, 26, 1353 and D. C. Atkinson, K. E. Godfrey, P. L. Meyers, N. C. Phillips, M. R. Stillings and A. P. Welbourn, *J.Med.Chem.*, 1983, 26, 1361. Furthermore, many of the methods described for the preparation of 2-arylpropionic esters and acids by J. P. Rieu, A. Boucherle, H. Cousse and G. Mouzin, *Tetrahedron*, 1986, 42, 4095, are also applicable to the preparation of phenylacetates of formula (III) and phenylacetic acids of formula (VII) using appropriate precursors wherein the ortho substituted phenoxy substituent and the substituent Z are already present.

Scheme I
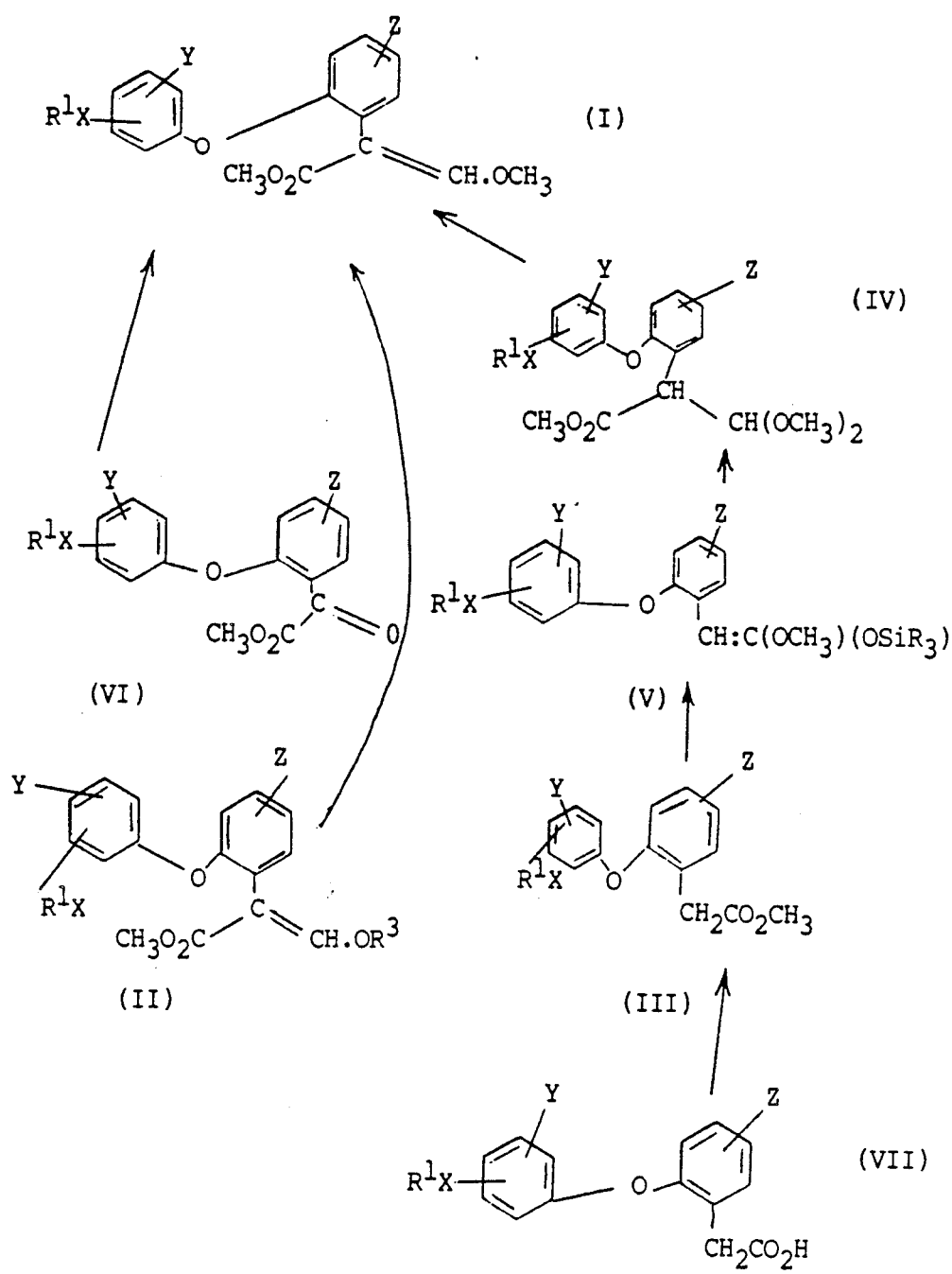
Scheme II
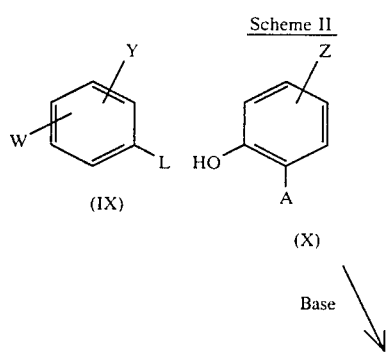
-continued
Scheme II
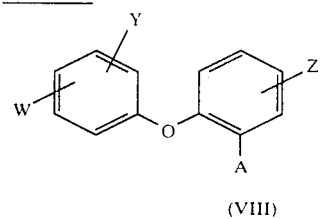

-continued
Scheme II (XI) — Y-substituted phenol with W and OH
(XII) — Z-substituted aryl with L and Y, Base Schemes III, IV and V illustrate examples of intermediates containing the methyl beta-methoxypropenoate group and show how they may be converted into certain specific types of compound of the invention (I).

Thus, in the presence of a base, compounds of formula (XIII) react with compounds of general formula $R^1L$ to give compounds of formula (XIV) (Scheme III).

The thiols of formula (XV), generally in the presence of a base, react with compounds of general formula $R^1L$ to give compounds of general formula (XVI) (Scheme IV). The sulphides of general formula (XVI) can be oxidised to the corresponding sulphoxides and sulphones by standard methods described in the chemical literature.

Similarly, amines of general formula (XVII), generally in the presence of a base, react with compounds of general formula $R^1L$ to give compounds of general formula (XVIII) (Scheme V).

The intermediates of formulae (XIII), (XV), and (XVII) can be prepared by processes described in the chemical literature (see, for example, EP-A-0307103) and by processes of the kinds described in Schemes I and II.

The intermediates of formulae (IX), (X), (XI), (XII) and $R^1L$ can be made by methods described in the chemical literature.

Scheme III (XIII) HO—aryl—O—aryl(Z)—C(CO$_2$CH$_3$)=CH.OCH$_3$ $R^1$—L (XIV) $R^1$O—aryl(Y)—O—aryl(Z)—C(CO$_2$CH$_3$)=CH.OCH$_3$ Scheme IV (XV) HS—aryl(Y)—O—aryl(Z)—C(CO$_2$CH$_3$)=CH.OCH$_3$ $R^1L$ (XVI) $R^1$S—aryl(Y)—O—aryl(Z)—C(CO$_2$CH$_3$)=CH.OCH$_3$ Scheme V (XVII) $R^2$NH—aryl(Y)—O—aryl(Z)—C(CO$_2$CH$_3$)=CH.OCH$_3$ $R^1L$ (XVIII) $R^1R^2$N—aryl(Y)—O—aryl(Z)—C(CO$_2$CH$_3$)=CH.OCH$_3$ In a further aspect the invention provides processes as hereindescribed for preparing the compounds of formula (I). It also provides intermediate chemicals of formulae (II) to (VII).

The compounds are active fungicides and may be used to control one or more of the following pathogens:

*Pyricularia oryzae* on rice.

*Puccinia recondita, Puccinia striiformis* and other rust on wheat, *Puccinia hordei, Puccinia striiformis* and other rusts on barley, and rusts on other hosts, e.g. coffee, pears, apples, peanuts, vegetables and ornamental plants.

*Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines. *Helminthosporium* spp., *Rhynchosporium* spp., *Septoria* spp., *Pseudocercosporella herepotrichoides* and *Gaeumannomyces graminis* on cereals.

*Cercospora arachidicola* and *Cercosporidium personata* on peanuts and other *Cercospora* species on other hosts, for example, sugar beet, bananas, soya beans and rice.

*Botrytis cinerea* (grey mould) on tomatoes, strawberries, vegetables, vines and other hosts. *Alternaria* species on vegetables (e.g. cucumber), oil seed rape, apples, tomatoes and other hosts.

*Venturia inaequalis* (scab) on apples.

*Plasmopara viticola* on vines.

Other downy mildews such as *Bremia lactucae* on lettuce, *Peronospora* spp. on soya beans, tobacco, onions and other hosts and *Pseudoperonospora humuli* on hops and *Pseudoperonospora cubensis* on cucurbits *Phytophthora infestans* on potatoes and tomatoes and other *Phytophthora* spp. on vegetables, strawberries, avocado, pepper, ornamentals, tobacco, cocoa and other hosts.

*Thanatephorus cucumeris* on rice and other Rhizoctonia species on various host such as wheat and barley, vegetables, cotton and turf.

Some of the compounds may show a broad range of activities against fungi in vitro. They may also have activity against various post-harvest diseases of fruit (e.g. *Penicillium digitatum* and *italicum* and *Trichoderma viride* on oranges, *Gloesporium musarum* and bananas and *Botrytis cinerea* on grapes).

Further some of the compounds may be active as seed dressings against Fusarium spp., Septoria spp., Tilletia spp., (bunt, a seed borne disease of wheat), Ustilago spp., Helminthosporium spp. on cereals, *Rhizoctonia solani* on cotton and *Pyricularia oryzae* on rice.

The compounds can move locally in the plant tissue. Moreover, the compounds may be volatile enough to be active in the vapour phase against fungi on the plant.

The invention therefore provides a method of combating fungi, which comprises applying to a plant, to seed of a plant, or to the locus of the plant or seed, an effective amount of compound as hereinbefore defined, or a composition containing the same. Some of the compounds may have advantages with respect to improved crop safety.

The compounds may be used directly for fungicidal purposes but are more conveniently formulated into compositions using a carrier or diluent. The invention thus provides a fungicidal composition comprising a compound of general formula (I) as hereinbefore defined, and a fungicidally acceptable carrier or diluent.

Used as fungicides, the compounds can be applied in a number of ways. For example they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition.

The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, fuller's earth, gypsum, diatomaceous earth and china-clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders of water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally controlling a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium-, or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants e.g. wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95% suitably 10–85%, for example 25–60%, by weight of the active ingredient. After dilution to form aqueous preparations, suitable preparations may contain varying amounts of the active ingredient depending upon the intended purpose, but an aqueous preparation containing 0.00055 or 0.01% to 10% by weight of active ingredient may be used.

The compositions of this invention may contain other compounds having biological activity, e.g. compounds having similar or complementary fungicidal activity or which plant possess plant growth regulating, herbicidal or insecticidal activity.

The compositions of this invention may contain other compounds having biological activity, eg. compounds having similar or complementary fungicidal activity or which possess plant growth regulating, herbicidal or insecticidal activity. A fungicidal compound which may be present in the composition of the invention may be one which is capable of combating ear diseases of cereals (eg. wheat) such as *Septoria*, *Gibberella* and *Helminthosporium* spp., seed and soil-borne diseases and downy and powdery mildews on grapes and powdery mildew and scab on apple etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl-aluminium, fenarimol, iprodione, prothiocarb, procymidone, vinclozolin, penconazole, my- clobutanil, propamocarb, diniconazole, pyrazophos, ethirimol, ditalimfos, tridemorph, triforine, nuarimol, iminodi(octamethylene)diquanidine, buthiobate, propiconazole, 3-chloro-4-[4-methyl-2-(1H-1,2,4--triazol-1-ylmethyl) -1,3-dioxolan-2-yl]phenyl-4-chlorophenyl ether, prochloraz, flutriafol, hexaconazole, furconazole-cis, cyproconazole, terbuconazole, pyrrolnitrin, 1-[(2RS, 4RS; 2RS, 4RS)-4-bromo-2-(2,4-dichlorophenyl)tetrahydrofurfuryl]-1H-1,2,4-triazole 5-ethyl-5,8-dihydro-8-oxo (1,3)-dioxolo(4,5 g)guinoline-7-carboxylic acid, (RS)-1-amino propylphosphonic acid, 3-(2,4-dichlorophenyl) -2-(1H-1,2,4-triazol-1-yl) quinazolin-4(3H)-one, (RS)-4-(4-chlorophenyl)-2-phenyl-2(1H-1,2,4-triazol -1- yl-methyl)butyronitrile, (±)-2-(2,4-dichlorophenyl) -3-(1H-1,2,4-triazol-1-yl)propyl 1,1,2,2,--tetrafluoroethyl ether, 4-chlorobenzyl N-(2,4-dichlorophenyl) -2-(1H-1,2,4-triazol-1--yl) thioacetamidate, alpha-[N-(3-chloro-2,6-xylyl)-2-methoxyacetamido]-gamma-butyrolactone, di-2-pyridyl disulphide 1,1'-dioxide, (Z)-N-but-2-enyloxymethyl-2--chloro-2', 6'-diethylacetanilide, ethyl (Z)-N-benzyl-N-([methyl(methylthioethylideneaminooxycarbonyl) amino]thio)-beta-alaninate, pent-4-enyl N-furfuryl-N-imidazol-1-ylcarbonyl-DL-homoalaninate, metsulfovax, fluzilazole, triadimefon, triadimenol, diclobutrazol, fenpropimorph, pyrifenox, fenpropidin, chlorozolinate, imazalil, fenfuram, carboxin, oxycarboxin, methfuroxam, dodemorph, BAS 454, blasticidin S, kasugamycin, edifenphos, iprobenfos, cycloheximide, phthalide, probenazole, isoprothiolane, tricyclazole, (RS)-4-chloro-N-(cyano(ethoxy)methyl) benzamide, pyroquilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofos-methyl, pyroxyfur, polyram, maneb, mancozeb, captafol, chlorothalonil, anilazine, thiram, captan, folpet, zineb, propineb, sulphur, dinocap, dichlone, chloroneb, binapacryl, nitrothal-isopropyl, dodine, dithianon, fentin hydroxide, fentin acetate, tecnazene, quintozene, dicloran, copper containing compounds such as copper oxychloride, copper sulphate and Bordeaux mixture, and organomercury compounds. The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (eg. grasses). Examples of suitable plant growth regulating compounds for use with the invention compounds are the gibberellins (eg. $GA_3$, $GA_4$ or $GA_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), glyphosate, glyphosine, long chain fatty alcohols and acids, dikegulac, paclobutrazol, fluoridamid, mefluidide, substituted quaternary ammonium and phosphonium compounds (eg. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat, benzoylprop-ethyl 3,6-dichloropicolinic acid, fenpentezol, inabenfide, triapenthenol and tecnazene.

The following Examples illustrate the invention. Throughout the Examples, the term 'ether' refers to diethyl ether, magnesium sulphate was used to dry solutions, and solutions were concentrated under reduced pressure. Reactions involving water-sensitive intermediates were performed under an atmosphere of nitrogen and solvents were dried before use, where appropriate. Unless otherwise stated, chromatography was performed on a column of silica gel as the stationary phase. Where shown, infrared and n.m.r. data are selective; no attempt is made to list every absorption in all cases. $^1$H n.m.r. spectra were recorded using CDCl$_3$-solutions unless otherwise stated. The following abbreviations are used throughout:

| | |
|---|---|
| THF = tetrahydrofuran | s = singlet |
| DMF = N,N-dimethylformamide | d = doublet |
| n.m.r. = nuclear magnetic resonance | t = triplet |
| | q = quartet |
| IR = infrared | m = multiplet |
| m.p. = melting point | br = broad |

EXAMPLE 1

This Example illustrates the preparation of (E)-methyl 2-[2-(3-allyloxyphenoxy)phenyl]-3-methoxypropenoate (Compound No 1 of Table 1). (E)-Methyl 2-2-(3-hydroxyphenoxy)phenyl]-3-methoxypropenoate (0.5g, prepared as described in Example 1 of EP-A-0307103), allyl bromide (0.8 g) and potassium carbonate (0.929) were stirred together in dry DMF (15 ml) at 50° C. for 3 hours. The reaction mixture was cooled, diluted with water and then extracted with ether (x2). The combined ether layers were washed with water (x3) and brine (x1), dried, filtered and evaporated to afford an oil (0.58 g). Chromatography on silica gel (eluent ether-hexane) afforded the title compound as an oil (0.53g, 94%);

$^1$H n.m.r. delta: 3.6 (3H,s); 3.77 (3H,s); 4.46 (1H,t) 4.52 (1H.t); 5.21-5.5 (2H,m); 5.86-6.21 (1H,m) 6.5-7.39 (8H,m); 7.47 (1H,s) ppm.

EXAMPLE 2

This Example illustrates the preparation of (E)--methyl 2-[2-(3-[ethoxycarbonylmethoxy]phenoxy)-phenyl]-3-methoxypropenoate (Compound No 41 of Table I).

A solution of (E)-methyl 2-[2-(3-hydroxyphenoxy)-phenyl]-3-methoxypropenoate (1.00 g), prepared as described in Example 1) in DMF (5 ml) was added dropwise over 10 minutes to a stirred suspension of sodium hydride (0.085 g) in DMF (15 ml). After 30 minutes, a solution of ethyl chloroacetate (0.8 g) in DMF (5 ml) was added dropwise over 10 minutes and the resulting mixture was stirred for 2 hours, then poured into brine and extracted with ethyl acetate (2 ×25 ml). The combined extracts were washed with water (2 ×25 ml) then dried, concentrated and chromatographed on silica gel (eluent ethyl acetate-hexane, 1:1) to give the title compound as a clear gum (0.68 g, 53%).

$^1$H n.m.r. (270MHz) delta: 1.28 (3H,t), 3.61 (3H,s), 3.78 (3H,s), 4.26 (2H,q), 4.54 (2H,s), 6.50-6.60 (3H,m),
6.93-6.98 (1H,m), 7.10-7.20 (2H,m), 7.22-7.30 (2H,m),
7.48 (1H,s)ppm.

EXAMPLE 3

This Example illustrates the preparation of (E)-methyl 2-[2-(3-[propargylamino]phenoxy)phenyl]-3-methoxypropenoate (Compound No 39 of Table I). (E)-Methyl 2-[2-(3-formamidophenoxy)phenyl]-3-methoxypropenoate (0.5 g, prepared as described in Example 31 of EP-A-0307103) in DMF (5 ml) was added to a suspension of sodium hydride (0.4 g) in DMF (10 ml) at room temperature. After 3 hours it was cooled to 0° C. and propargyl bromide (0.22 ml of an 80% solution in toluene) was added. The mixture was stirred for 16 hours, then poured into water (100 ml) and extracted with ether (2×50 ml). The combined extracts were washed with brine, then dried and concentrated to give a brown oil. This oil was dissolved in methanol (20 ml) and treated dropwise with phosphoryl chloride (0.2 ml). After 5 minutes, the resulting mixture was poured into water (100 ml), neutralised with sodium bicarbonate and then extracted with ether (2×50 ml). The combined extracts were dried, concentrated and chromatographed (eluant ether) to give the title compound (0.154g, 30%) as a clear oil.

$^1$H n.m.r. (270 MHz) delta: 2.20 (1H,m), 3.62 (3H,s), 3.74 (3H,s), 3.85 (2H,brs), 4.9 (1H,brs), 6.25-6.40 (3H,m), 6.90-7.30 (5H,m), 7.47 (1H,s)ppm.
IR maxima (film): 3389, 3284, 1702, 1635, 1609 cm$^{-1}$.

The following are examples of compositions suitable for agricultural and horticultural purposes which can be formulated from the compounds of the invention. Such compositions from another aspect of the invention. Percentages are by weight.

EXAMPLE 4

An emulsifiable concentrate is made up by mixing and stirring the ingredients until all are dissolved.

| | |
|---|---|
| Compound No. 3 of Table 1 | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 5

The active ingredient is dissolved in methylene dichloride and the resultant liquid sprayed on to the granules of attapulgite clay. The solvent is then allowed to evaporate to produce a granular composition.

| | |
|---|---|
| Compound No. 3 of Table I | 5% |
| Attapulgite granules | 95% |

EXAMPLE 6

A composition suitable for use as a seed dressing is prepared by grinding and mixing the three ingredients.

| Compound No. 3 of Table I | 50% |
| --- | --- |
| Mineral oil | 2% |
| China clay | 48% |

EXAMPLE 7

A dustable powder is prepared by grinding and mixing the active ingredient with talc.

| Compound No. 3 of Table I | 5% |
| --- | --- |
| Talc | 95% |

EXAMPLE 8

A suspension concentrate is prepared by ball milling the ingredients to form an aqueous suspension of the ground mixture with water.

| Compound No. 3 of Table I | 40% |
| --- | --- |
| Sodium lignosulphonate | 10% |
| Bentonite clay | 1% |
| Water | 49% |

This formulation can be used as a spray by diluting into water or applied directly to seed.

EXAMPLE 9

A wettable powder formulation is made by mixing together and grinding the ingredients until all are thoroughly mixed.

| Compound No. 3 of Table I | 25% |
| --- | --- |
| Sodium lauryl sulphate | 2% |
| Sodium lignosulphonate | 5% |
| Silica | 25% |
| China clay | 43% |

EXAMPLE 10

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

4 = no disease
3 = trace-5% of disease on untreated plants
2 = 6-25% of disease on untreated plants
1 = 26-59% of disease on untreated plants
0 = 60-100% of disease on untreated plants

TABLE IV

| COMPOUND NO (TABLE I) | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INFESTANS LYCOPERSICI (TOMATO) |
| --- | --- | --- | --- | --- | --- | --- | --- |
| 1 | 2 | 4 | 4 | — | 4 | — | 4 |
| 2 | 4 | 4 | 4 | 4 | 4 | 4 | 4 |
| 3 | 4 | 4 | 4 | 3 | 3 | 4 | 4 |
| 4 | 4 | 4 | 4 | 4 | 4 | 4 | 4 |
| 9 | 4 | 4 | 4 | 1 | 3 | 4 | 4 |
| 10 | 4 | 4 | 4 | 0 | 3 | 4 | 3 |
| 11 | 0 | 0 | 0 | 0 | 0 | 4 | 1 |
| 29 | 4 | 4 | 4 | 3 | — | 4 | 4 |
| 38 | 4 | 4 | 4 | — | — | 4 | 2 |
| 39 | — | 3 | 4 | 3 | 4 | 4 | 4 |
| 40 | 3 | 1 | 4 | 2 | 3 | 4 | 3 |
| 41 | 3 | 0 | 4 | 0 | 0 | 4 | 3 |

—no result

What we claim is :

1. Fungicidal compounds of the formula (I) :

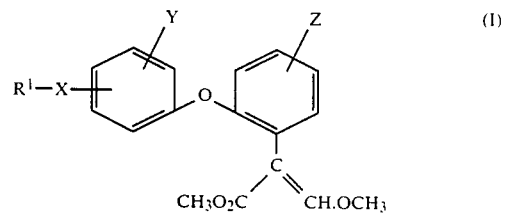

and stereoisomers thereof, wherein $R^1$ is optionally substituted $C_{2-10}$ alkenyl, optionally substituted $C_{5-6}$ cycloalkenyl, optionally substituted $C_{2-10}$ alkynyl, or $C_{1-10}$ alkyl substituted with —CN, —NC, —COR$^2$, —CO$_2$R$^2$, —NO$_2$ or —SCN; X is O, S(O)n or NR$^2$ and is attached to the 3- or the 4-position of the phenyl ring; Y and Z, which may be the same or different, are H, halogen, —CH$_3$, —C$_2$H$_5$, or —OCH$_3$; R$^2$ is H, C$_{1-4}$ alkyl, C$_{1-4}$ alkenyl, or, when R$^2$ is C$_{1-4}$ alkyl in the group —COR$^2$, it joins with the alkyl group to which —COR$^2$ is attached to form a 5- or 6-membered aliphatic ring; and n is 0, 1 or 2.

2. A compound according to claim 1 wherein $R^1$ is $C_{2-10}$ alkenyl or $C_{2-10}$ alkynyl, X is O and Y and Z are H, halogen, —$CH_3$, —$C_2H_5$ or —$OCH_3$.

3. A compound according to claim 2 wherein $R^1$ is alkynyl and Y and Z are H.

4. A compound according to claim 3 wherein $R^1$ is —$CH_2$ CH≡CH

5. A compound according to claim 4 wherein X is attached to the 4- position.

6. A fungicidal composition comprising a fungicidally effective amount of a compound according to claim 1 and a fungicidally acceptable carrier or diluent therefor.

7. A method of combating fungi which comprises applying to plants, to the seeds of plants or to the locus of the plants or seeds, an effective amount of a compound according to claim 1.

* * * * *